United States Patent [19]

Mehta et al.

[11] Patent Number: 4,794,001

[45] Date of Patent: Dec. 27, 1988

[54] FORMULATIONS PROVIDING THREE DISTINCT RELEASES

[75] Inventors: Atul M. Mehta, Ramsey, N.J.; Lizbeth A. Bachand; Thomas W. Leonard, both of Plattsburgh, N.Y.; Ronald N. Warner, Grand Isle, Vt.

[73] Assignee: American Home Products Corporation, New York, N.Y.

[21] Appl. No.: 100,646

[22] Filed: Sep. 24, 1987

Related U.S. Application Data

[60] Division of Ser. No. 836,033, Mar. 4, 1986, Pat. No. 4,728,512, which is a continuation-in-part of Ser. No. 731,175, May 6, 1985, abandoned.

[51] Int. Cl.⁴ .................... A61K 9/52; A61K 9/54; A61K 9/58
[52] U.S. Cl. ........................ 424/458; 424/453; 424/457; 424/459; 424/461; 424/462
[58] Field of Search .............. 424/458, 453, 457, 459, 424/461, 462

[56] References Cited

U.S. PATENT DOCUMENTS

| | | | |
|---|---|---|---|
| 2,809,918 | 10/1987 | Hermelin | 424/19 |
| 2,921,883 | 1/1960 | Reese et al. | 424/19 |
| 2,951,792 | 9/1960 | Swintosky | 167/82 |
| 3,044,938 | 7/1962 | Halley | 167/82 |
| 3,074,852 | 1/1963 | Mayron | 167/82 |
| 3,119,742 | 1/1964 | Heimlich et al. | 424/19 |
| 3,175,521 | 3/1965 | Hershberg | 424/14 |
| 3,325,365 | 6/1967 | Hotko | 167/82 |
| 3,558,768 | 1/1971 | Klippel | 424/21 |
| 3,835,221 | 9/1974 | Fulberth et al. | 424/19 |
| 3,859,431 | 1/1975 | Newton et al. | 424/37 |
| 4,138,475 | 2/1979 | McAinsh et al. | 424/21 |
| 4,173,626 | 11/1979 | Dempski et al. | 424/20 |
| 4,248,856 | 2/1981 | Guley et al. | 424/19 |
| 4,248,857 | 2/1981 | DeNeale et al. | 424/21 |
| 4,248,858 | 2/1981 | Guley et al. | 424/21 |
| 4,294,819 | 10/1981 | Tencza, II | 424/14 |
| 4,309,404 | 1/1982 | DeNeale et al. | 424/21 |
| 4,309,405 | 1/1982 | Guley et al. | 424/21 |
| 4,309,406 | 1/1982 | Guley et al. | 424/21 |
| 4,339,428 | 7/1982 | Tencza, I | 424/21 |
| 4,524,060 | 6/1985 | Mughal et al. | 424/22 |

FOREIGN PATENT DOCUMENTS

| | | | |
|---|---|---|---|
| 1204580 | of 1910 | United Kingdom | 424/37 |
| 2039737 | 8/1980 | United Kingdom | 354/193 |

OTHER PUBLICATIONS

F. W. Goodhart et al., Pharmaceutical Technology, pp. 64–71, Apr. 1984.

*Primary Examiner*—Shep K. Rose
*Attorney, Agent, or Firm*—John W. Routh

[57] ABSTRACT

A therapeutic preparation consisting of three groups of spheroids containing an active medicinal substance. The first group of spheroids is uncoated and rapidly disintegrates upon ingestion to release an initial dose of medicinal substance a second group of spheroids is coated with a pH sensitive coat to provide a second dose and a third group of spheroids is coated with a pH independent coat to provide a third dose. A powder blend of active medicinal substance may be substituted for the first group of uncoated spheroids.

The therapeutic preparation may be utilized as a mixture of groups of spheroids in a capsule.

8 Claims, 6 Drawing Sheets

FORMULATIONS PROVIDING THREE DISTINCT RELEASES

This is a division of application Ser. No. 836,033, filed Mar. 4, 1986, now U.S. Pat. No. 4,728,512, which is a continuation-in-part of application Ser. No. 731,175, filed May 6, 1985, now abandoned.

BACKGROUND OF THE INVENTION

This invention relates to pharmaceutical preparations for oral administration encapsulated in a capsule dosage form and more particularly relates to such therapeutic preparations comprising coated pellets or spheroids which release a dose of an active medicinal substance at different times in the digestive system of a patient.

Timed disintegration capsules for the sequential, timed release of medicinal substances into a patient's system are known in the art. Generally such capsules or tablets consist of particles containing the medicinal substance to be introduced into the system, and a coating over the particles of a material which is resistant to disintegration for a selected period of time. Such coating compositions are also referred to as enteric coating compositions, that is, compositions which are generally resistant to disintegration in the stomach, but which disintegrate in the intestine. Enteric compositions also include compositions which disintegrate slowly in the stomach such that the medicinal substance is not released until the capsule or tablet has reached the intestine of the patient. For example, coatings comprising bees wax and glyceryl monostearate; bees wax, shellac and cellulose; and cetyl alcohol, mastic and shellac have been proposed for use as slow release or timed release coatings for medicinal substances. Release of the medicinal substance by disintegration of the coating is generally controlled by varying the thickness of the coating or by altering its composition.

U.S. Pat. No. 2,809,918 discloses inert drug coated nonpareils which are enteric coated with a shellac-stearic acid mixture. U.S. Pat. No. 3,119,742 discloses coated drug crystals used as particulates for sustained release formulations. U.S. Pat. No. 2,921,883 discloses "Spansule," nonenteric coated spheroids designed for sustained release. U.S. Pat. No. 3,835,221 discloses oral delayed action "globules" coated with a mixture of polyvinylacetate and ethyl cellulose, useful as an "inert carrier core." F. W. Goodhart et al., Pharmaceutical Technology, page 64–71, April 1984, discloses the evaluation of Eudragit E 30 D as an aqueous film forming dispersion for controlled release of phenylpropanolamine hydrochloride.

The prior art compositions have generally proved deficient in the case where the medicinal substance is extensively metabolized presystemically or has a relatively short elimination half-life resulting in subtherapeutic plasma levels. Also, with many patients, the coatings are not disintegrated to the extent necessary to release the medicinal substance until the tablet or capsule has reached the colon and the medicinal substance is discharged from the system rather than absorbed by the intestine.

The present invention provides three repeated releases of a medicinal substance for once daily administration of those medicinal substances which are extensively metabolized presystemically or have relatively short elimination half-lives. This system results in superior oral bioavailability as compared to a continuous release system for a medicinal substance over a 6 to 24 hour period. The present invention also provides the convenience of not requiring the administration of divided doses during a 24 hour period and results in better patient compliance.

The medicinal agents useful in the invention are those that exhibit a significant presystemic metabolism or have a relatively short elimination half life that normally would be administered in divided doses two or more times a day. Such medicinal agents include the cardiovascular drugs such as propranolol hydrochloride, isosorbide dinitrate, isosorbide-5-mononitrate, pelrinone (see U.S. Pat. No. 4,505,910), acifran (see U.S. Pat. No. 4,244,958) verapamil hydrochloride, quinidine sulfate, the cerebral activators such as vinpocetine, Ay-30109 (see U.S. patent application Ser. No. 811,551, filed Dec. 20, 1985 by Jirkovsky et al., entitled 6,7,8,9-Tetrahydro-10-methylpyrido[1,2-a]indole-9-Amines and Derivatives Thereof (AHP-8728); the analgesics such as those disclosed and claimed in U.S. patent application Ser. No. 726,197, filed Apr. 22, 1985, the antihistamines such as chlorpheniramine and bromopheniramine; and the decongestants such as pseudoephedrine and phenylpropanolamine.

In the case of medicinal agents having a significant pH dependent solubility profile, weak organic acids such as citric, tartaric, fumaric and glutamic acids may be added to the spheroid formulation to facilitate drug dissolution throughout the gastrointestinal tract.

The present invention also lies in the general area of timed disintegration coatings and represents a substantial improvement over the prior art compositions in that the time of disintegration is readily controllable and easily adjusted for release of a medicinal substance.

The present invention relates to a therapeutic composition comprising a pharmaceutical gelatin capsule containing (i) a powder blend of a medicinal substance and two groups of spheroids each containing the medicinal substance or (ii) three groups of spheroids each containing a medicinal substance, the alternative group of spheroids comprising uncoated spheroids containing a loading dose of the medicinal substance. In each embodiment, the second group of spheroids comprises pH sensitive coated spheroids containing a second dose of the medicinal substance and the third group of spheroids comprises double coated spheroids containing a third dose of the medicinal substance.

A further preferred aspect of the present invention relates to a therapeutic composition consisting of a pharmaceutical gelatin capsule containing three groups of spheroids wherein, (a) the first group of spheroids comprises an active medicinal substance admixed with non-water swellable microcrystalline cellulose, (b) the second group of spheroids comprises the medicinal substance in admixture with non-water swellable microcrystalline cellulose and is coated with a copolymer based on methacrylic acid and methacrylic acid methyl ester such as Eudragit S to the extent of 20% to 30% by weight of uncoated spheroids or polyvinyl acetate phthalate to the extent of 5% to 15% by weight of uncoated spheroids and preferably to the extent of 10% by weight and (c) the third group of spheroids comprises the medicinal substance in admixture with non-water swellable microcrystalline cellulose and is coated with (i) an undercoat to the extent of 2.5% to 5.5% by weight of uncoated spheroids selected from the group consisting of hydroxypropyl methylcellulose and hydroxypropyl methylcellulose containing as a disintegrant sodium carboxymethylcellulose, such as AcDiSol, or sodium starch glycolate such as Explotab, wherein the AcDiSol is present to the extent of 10% to 60% by weight of the hydroxypropyl methylcellulose and the Explotab is present to the extent of 10% to 60% by weight of the hydroxypropyl methyl cellulose and an (i) overcoat comprising a neutral copolymer of polymethacrylic acid esters such as Eudragit E30D containing metallic stearates wherein the Eudragit E30D is present to the extent of 5% to 12% by weight of the uncoated spheroids and the metallic stearate is present to the extent of 9% to 16% by weight of the Eudragit E30D solids and preferably about 12.5% by weight of the Eudragit E30D solids.

A separate and distinct aspect of the present invention relates to the double coated spheroids used as the third dose of the active medicinal substance.

Suitable pharmaceutical excipients for the powder blend of the medicinal substance include lactose, microcrystalline cellulose, starch, calcium phosphate, calcium sulfate, stearic acid, magnesium stearate and disintegrants.

Eudragit S is a copolymer, anionic in character, based on methacrylic acid and methacrylic acid methyl ester. The ratio of free carboxylic groups to the esters is approximately 1:2. The mean molecular weight is 135,000. Eudgragit S is available as a lacquer solution in isopropyl alcohol and as a solvent free solid. It is known as methacrylic acid copolymer, Type B, N.F.

Eudragit E30D is a copolymer, neutral in character, based on polymethacrylic acid esters. The mean molecular weight is 800,000. Eudragit E 30 D is available as a 30% (28.5%–31.5%) aqueous dispersion. Both Eudragit S and Eudragit E30D are available from Rohm Pharma, D-6108 Weiterstadt 1, Dr.-Otto-Rohm-Str. 2-4, West Germany.

Metalic stearates include zince stearate, calcium stearate and magnesium stearate.

Explotab is a trade name for sodium starch glycolate. Sodium starch glycolate is the sodium salt of a carboxymethyl ether of starch. It is available from Edward Mendell Co., Inc., Route 52, Carmel, N.Y. 10512, U.S.A.

AcDiSol is a trade name for carboxymethylcellulose sodium. It is the sodium salt of a polycarboxymethyl ether of cellulose, available from FMC Corporation, 200 Market St., Philadelphia, Pa. 19103, U.S.A.

Other disintegrants such as Amberlite can be used instead of Explotab and AcDiSol.

Suitable grades of hydroxypropyl methylcellulose for use in the present invention are the Methocel brand, made by Dow Chemical Comany, Midland, Mich., U.S.A., grades E, F and K having a viscosity range of about 3500 to about 5600 cps and preferably a viscosity of about 4000 cps.

Also suitable grades of hydroxypropyl methylcellulose are the Metolose brand, made by Shin-Etsu Chemical Co., Ltd., grades 60 SH, 65 SH and 90 SH having a viscosity range of about 3500 to about 5600 cps and preferably a viscocity of about 4000 cps.

Methocel F is a grade of hydroxypropyl methylcellulose containing about 27 to 30% methoxyl content and from about 4.0 to 7.5% hydroxypropoxyl content calculated on the dried basis. Methocel K is a grade of hydroxypropyl methylcellulose containing about 19 to 25% methoxyl content and from about 4 to 12% hydroxypropoxyl content calculated on the dried basis.

The preferred grade of hydroxypropyl methylcellulose for use in the present invention is hydroxypropyl methylcellulose USP, 2910, 4000 cps (METHOCEL E4MP) which is a propylene glycol ether of methylcellulose contaning not less than 28.0% and not more than 30.0% methoxyl content, and not less than 7.0% and not more than 12.0% hydroxypropoxyl content.

A suitable non-water swellable microcrystalline cellulose is, for example, the material sold as Avicel-PH-101 (available from FMC Corporation, American Viscose Division, Avicel Sales, Marcus Hook, Pa., U.S.A.).

The polyvinyl acetate phthalate, available from Colorcon, Inc., is the standard grade.

The spheroid coatings may further contain other pharmaceutically acceptable excipients such as binders, fillers, anti-adherents and the like.

A still further preferred aspect of the present invention relates to a therapeutic composition comprising a pharmaceutical hard gelatin capsule containing three groups of spheroids containing an active medicinal substance, wherein (a) the first group of spheroids comprising uncoated spheroids contains the medicinal substance for maximum release thereof within a period of two hours after ingestion, (b) the second group of spheroids comprising coated spheroids contains the medicinal substance in a spheroid core coated with a pH sensitive coat comprising a copolymer based on methacrylic acid and methacrylic acid methyl ester or polyvinyl acetate phthalate, the coat having and effective thickness to provide a maximum release of medicinal substance in a period of 2 to 6 hours after ingestion, and (c) the third group of spheroids comprising coated spheroids contains medicinal substance in a spheroid core coated with an undercoat of hydroxypropyl methylcellulose and an overcoat of a neutral copolymer based on polymethacrylic acid esters containing metallic stearates, the coats having an effective thickness to provide a maximum release of medicinal substance 4 to 10 hours after ingestion.

The following examples are by way of illustration of the preferred embodiments of the therapeutic preparation of the present invention and its manner of preparation.

In the first four of these examples, the uncoated spheroids were made in accordance with the teachings of U.S. Pat. No. 4,138,475 in the following manner:

Propranolol hydrochloride (60 kg.) and microcrystalline cellulose (Avicel-PH-101; 40 kg.) were blended together in a 450 liter planetary mixer. Water (50 kg.) was added, and the mixer was run for 10 minutes until a homogeneous, plastic mass was obtained. The mass was extruded under pressure through a perforated cylinder to give cylindrical extrudates of nominally 1 mm. diameter.

The damp extrudates (in batches of 15 to 20 kg.) were placed in a spheronizer in which the rotating disc (diameter 68 cm.) rotated at 300 to 400 r.p.m. The rotation was continued for 10 minutes, and the resulting spheroids were then dried at 60° C. in a fluidized bed drier. The dried spheroids were passed over a 1.4 mm. screen, and those which passed through were subjected to a 0.7 mm. screen. The over-and under-sized spheroids were discarded.

EXAMPLE 1

The finished dosage form consists of a hard gelatin capsule containing a power blend of propranolol hydrochloride and two types of spheroids. The formulation particulars are based on 160 mg propranolol hydrochloride per capsule, although they can be designed to provide other dosage strengths.

The propranolol hydrochloride powder blend (or first group of spheroids) provides the loading dose, (e.g. 25 mg propranolol HCl).

The second and third types of spheroids are categorized as:

(1) pH sensitive coated spheroids to provide a second dose (pH>6.5) e.g. 65 mg propranolol HCl.
(2) Coated spheroids to provide a third dose (4–10 hours post ingestion) e.g. 70 mg propranolol HCl.

1. Powder Blend
(a) Formula

| Ingredient | Quantity |
|---|---|
| Propranolol HCl, USP | 30 mg/capsule |
| Lactose, USP | 54 mg/capsule |
| Microcrystalline cellulose, NF | 15 mg/capsule |
| Magnesium stearate, NF | 1 mg/capsule |

2. pH Sensitive Coated Spheroids
(i) Eudragit S System:
(a) Formula (based on 3 kg uncoated spheroids)

| Ingredients | Quantity |
|---|---|
| Uncoated Spheroids (60% w/w Propranolol HCl) | 3.00 kg |
| Methacrylic Acid Copolymer, Type B, NF Eudragit S | 0.75 kg |
| Triacetin, USP | 0.112 kg |
| Methylene Chloride, NF | 1.99 kg |
| Isopropyl Alcohol, USP | 1.64 kg |
| Water | 0.50 kg |

(b) Process
Uncoated spheroids were placed in a fluidized bed coater
The Eudragit S solution was applied using a peristaltic pump
The spheroids were dried 3. Coated Spheroids
(a) Formula (based on 3 kg uncoated spheroids)

| | Quantity |
|---|---|
| Undercoat Ingredients | |
| Uncoated Spheroids (60% w/w propranolol HCl) | 3.00 kg |
| Hydroxypropyl methylcellulose, USP, 2910, 4000 cps, (e.g., Methocel E4MP) | 0.075 kg |
| Methylene Chloride, NF | 4.987 kg |
| Methanol, Anhydrous, NF | 2.963 kg |
| Overcoat Ingredients | |
| Eudragit E 30 D (Aqueous Dispersion) | 1.00 kg |
| Calcium Stearate, NF | 0.030 kg |
| Simethicone Emulsion, USP | 0.0025 kg |
| Water, USP, Purified | 0.500 kg |

(b) Process for applying undercoat
The uncoated spheroids were placed in a fluidized bed coater
Methocel E4MP solution was sprayed using a peristaltic pump
The spheroids were dried
(c) Process for applying overcoat
Eudragit E 30 D suspension containing calcium stearate was sprayed on the Methocel E4MP coated spheroids using peristaltic pump
The spheroids were dried 4. Manufacture
Capsules were filled with the powder blend, pH-sensitive coated spheroids and coated spheroids on an encapsulating machine capable of dual filling powders and spheroids.

EXAMPLE 2

The finished dosage form consists of a hard gelatin capsule containing 3 types of spheroids. The formulation particulars are based on 160 mg propranolol HCl per capsule, although they can be designed to provide other dosage strengths.

The three types of spheroids are categorized as:
(1) Uncoated spheroids to provide a loading dose (e.g. 30 mg propranolol HCl)
(2) pH sensitive coated spheroids to provide a second dose (pH>5.5) e.g. 60 mg propranolol HCl
(3) Coated spheroids to provide a third dose (4–10 hours post ingestion) e.g. 70 mg propranolol HCl 1. Uncoated Spheroids (prepared as described previously)
2. Alternate pH Sensitive Coated Spheroids
Polyvinyl Acetate Phthalate (PVAP) system:
(a) Formula-(based on 3 kg uncoated spheroids)

| Ingredients | Quantity |
|---|---|
| Uncoated Spheroids (60% w/w propranolol HCl) | 3.00 kg |
| Polyvinyl Acetate Phthalate (PVAP), NF | 0.30 kg |
| Triethyl Citrate, NF | 0.03 kg |
| Stearic Acid, NF | 0.06 kg |
| Methanol, Anhydrous, NF | 2.61 kg |

(b) Process
Uncoated spheroids were placed in a fluidized bed coater
The PVAP solution was applied using a peristaltic pump
The spheroids were dried
3. Coated Spheroids (prepared as described above in Example 1)

EXAMPLE 3

1. Uncoated Spheroids (prepared as described above)
2. pH Sensitive Coated Spheroids (prepared as described above in Example 1)
3. Coated Spheroids
(a) Formula (based on 3 kg uncoated spheroids)

| | Quantity/Batch |
|---|---|
| Undercoat Ingredients | |
| Uncoated Spheroids (60% w/w propranolol HCl) | 3.0 kg |
| Hydroxypropyl methylcellulose, USP, 2910, 4000 cps (Methocel E4MP) | 0.075 kg |
| Methylene Chloride, NF | 4.987 kg |
| Methanol, Anhydrous, NF | 2.963 kg |
| Overcoat Ingredients | |
| Eudragit E 30 D (aqueous dispersion) | 0.600 kg |
| Calcium Stearate, NF | 0.0225 kg |
| Simethicone Emulsion USP | 0.002 kg |
| Water, USP, Purified | 0.300 kg |

(b) Process for applying undercoat

The uncoated spheroids were placed in a fluidized bed coater

Methocel E4MP solution was applied using a peristaltic pump

The spheroids were dried (c) Process for applying overcoat

Eudragit E 30 D suspension containing calcium stearate was sprayed on the Methocel E4MP coated spheroids using a peristaltic pump The spheroids were dried The three types of spheroids are categorized as:
(1) Uncoated spheroids to provide a loading dose (e.g. 30 mg propranolol HCl)
(2) pH sensitive coated spheroids to provide a second dose (pH 6.5) e.g. 60 mg propranolol HCl
(3) Coated spheroids to provide a third dose (4–10 hours post ingestion) e.g. 70 mg propranolol HCl

EXAMPLE 4

1. Uncoated Spheroids (prepared as described above)
2. pH Sensitive Coated Spheroids (prepared as described above in Example 1)
3. Coated Spheroids
(a) Formula

|  | Quantity/Batch |
| --- | --- |
| Undercoat Ingredients | |
| Uncoated Spheroids (60% w/w Propranolol HCl) | 3.00 kg |
| Hydroxypropyl methylcellulose, USP, 2910, 4000 cps (E4MP) | 0.075 kg |
| Methylene Chloride, NF | 4.987 kg |
| Methanol, Anhydrous, NF | 2.963 kg |
| Overcoat Ingredients | |
| Eudragit E 30 D (Aqueous Dispersion) | 0.550 kg |
| Calcium Stearate, NF | 0.021 kg |
| Simethicone Emulsion, USP | 0.002 kg |
| Water, USP, Purified | 0.275 kg |

(b) Process for applying undercoat

The uncoated spheroids were placed in a fluidized bed coater

Methocel E4MP solution was applied using a peristaltic pump

The spheroids were dried (c) Process for applying overcoat

Eudragit E 30 D suspension containing calcium stearate was sprayed on the Methocel E4MP coated spheroids using a peristaltic pump The spheroids were dried The three types of spheroids are categorized as:
(1) Uncoated spheroids to provide a loading dose (e.g. 30 mg proparanolol HCl)
(2) pH sensitive coated spheroids to provide a second dose (pH>6.5) e.g. 60 mg propanolol HCl
(3) Coated spheroids to provide a third dose (4–10 hours post ingestion) e.g. 70 mg propranolol HCl The finished dosage form consists of a hard gelatin capsule containing three types of spheroids containing propranolol hydrochloride. The formulation particulars are based on 160 mg propranolol hydrochloride per capsule, although they can be designed to provide other dosage strengths as follows:

| Propranolol Hydrochloride mg per capsule | First group of spheroids (or powder) % of dose | Second group of spheroids % of dose | Third group of spheroids % of dose |
| --- | --- | --- | --- |
| 40 to 240 | 10% to 30% | 20% to 75% | 10% to 60% |
| 160 | 12% to 20% | 35% to 45% | 35% to 45% |

Figure 1:
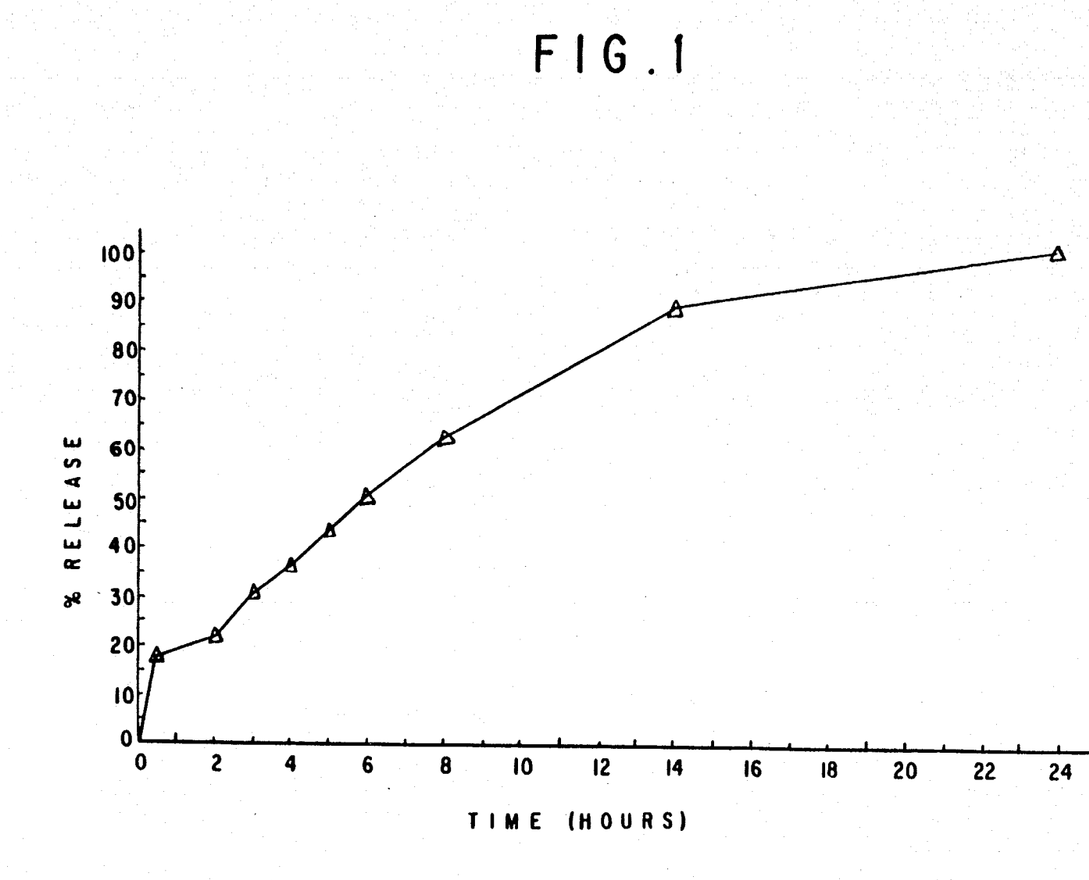

Examples of in vitro release profiles are given in FIGS. 1–4. FIG. 1 represents the dissolution profile of the composite capsule formulation comprised of three separate doses, produced in Example 3. The dissolution profile was obtained using the United States Pharmacopeia Apparatus I at 37° C. and 100 RPM. The dissolution media was varied with time beginning with 0.1N HCl for 0 to 2 hours. From 2 to 4 hours the media was pH 6.5 phosphate buffer and from 4 to 24 hours the media was pH 7.5 phosphate buffer.

Figure 2:
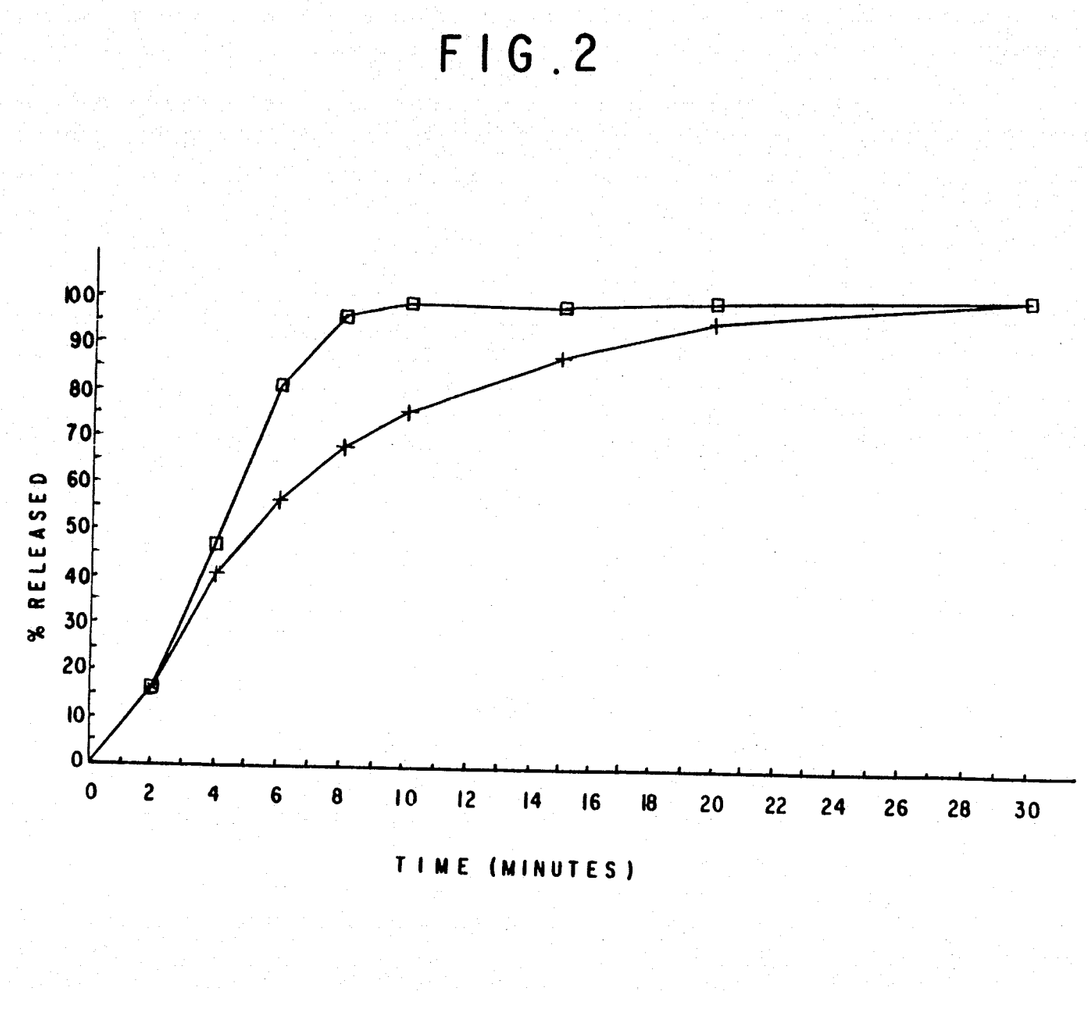

FIG. 2 represents the dissolution profiles of the first dose uncoated spheroids produced in Examples 2, 3 and 4 vs the powder blend of the first dose in Example 1. The dissolution profiles were obtained using the United States Pharmacopeia Apparatus I at 37° C. and 100 RPM. The dissolution media was 0.1N HCl.

Figure 3:
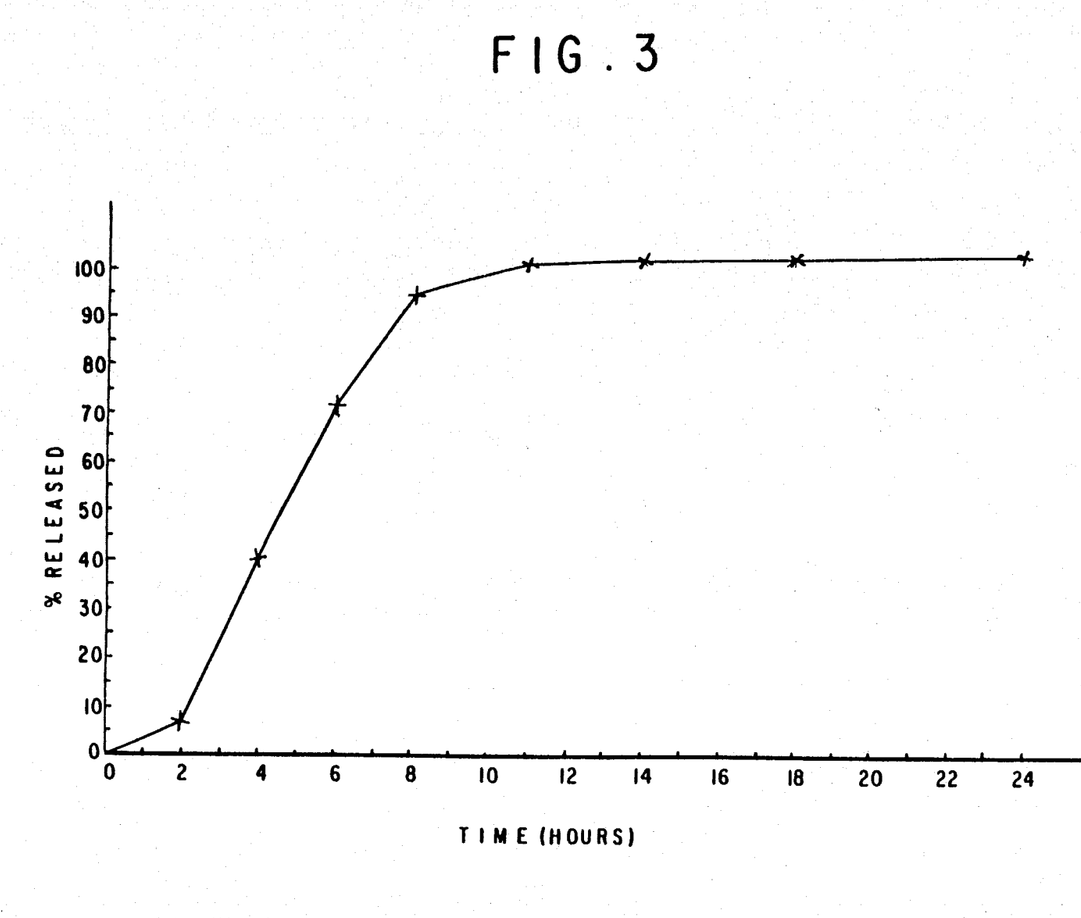

FIG. 3 represents the dissolution profile of the second dose Eudragit S coated spheroids produced in Example 1, 2, 3 and 4. The dissolution profile was obtained using the United States Pharmacopeia Apparatus I at 37° C. and 100 RPM. The dissolution media was varied with time beginning with 0.1N HCl from 0 to 2 hours. From 2 to 4 hours the media was pH 6.5 phosphate buffer and from 4 to 24 hours the media was pH 7.5 phosphate buffer.

Figure 4:
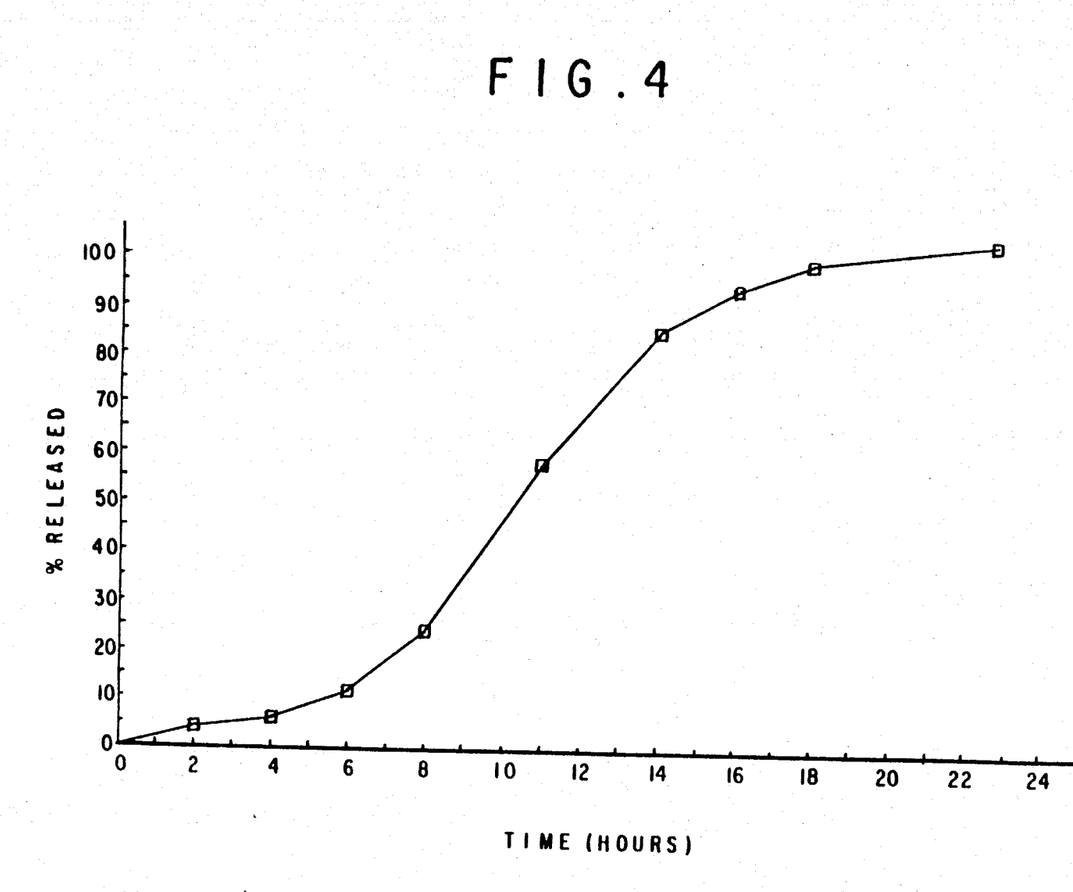

FIG. 4 represents the dissolution profile of the third dose produced in Example 3. The dissolution profile was obtained using a modification of the United States Pharmacopeia Apparatus I, at 37° C., 100 RPM, and water as the dissolution media.

Figure 5:
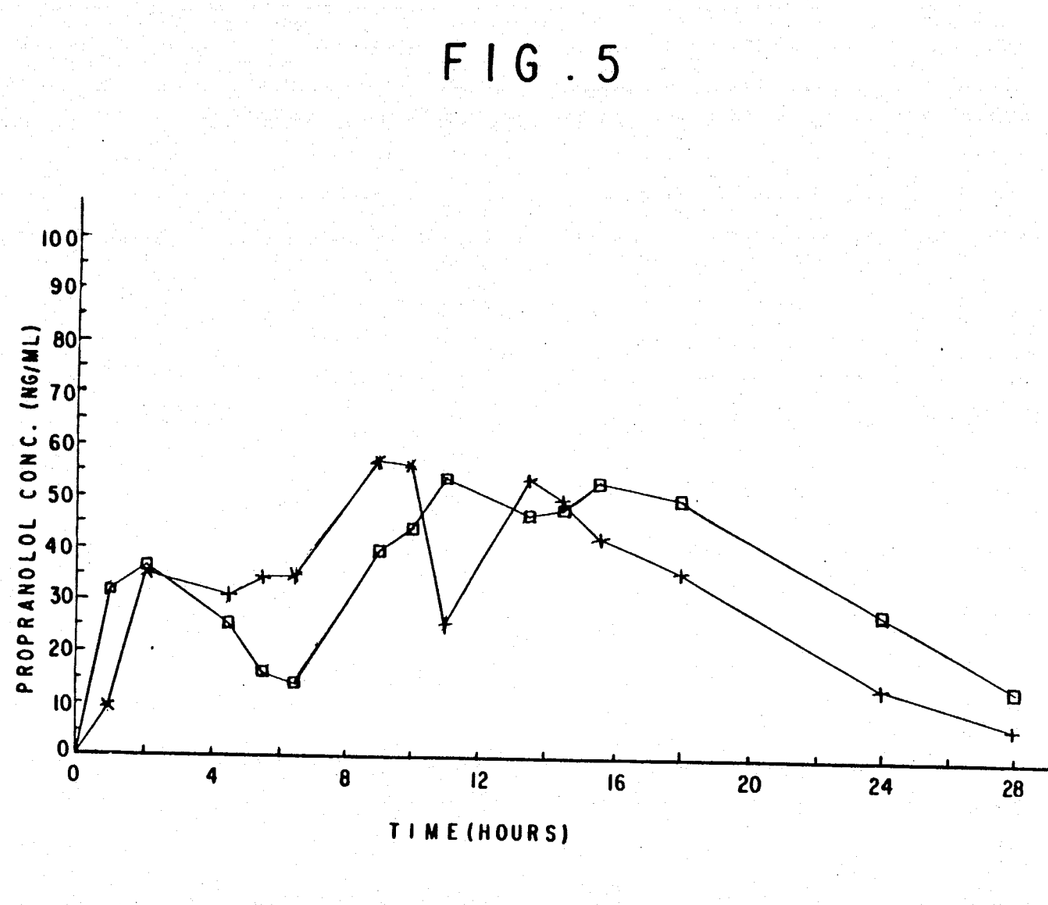
Figure 6:
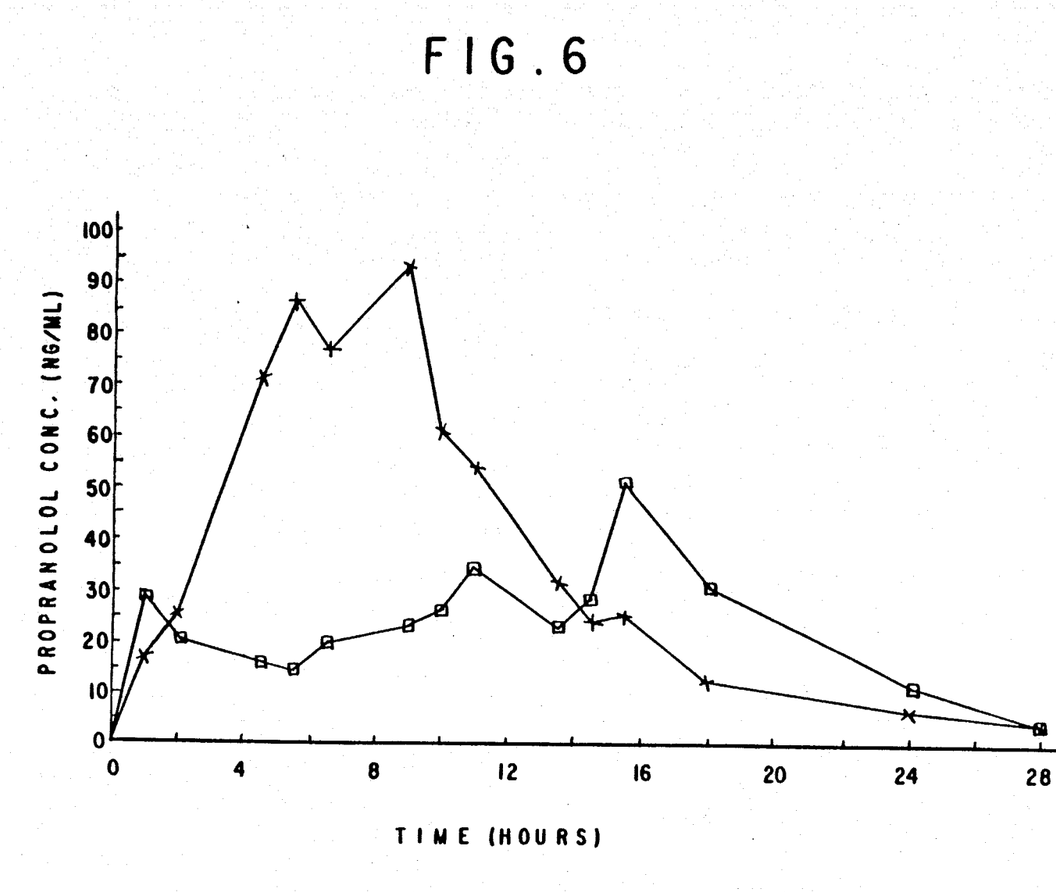

FIGS. 5 and 6 represent the in vivo profiles of propranolol hydrochloride in two different human subjects dosed once a day with the composite capsule containing a total of 160 mg propranolol hydrochloride (FIG. 1) vs a total of 160 mg propranolol hydrochloride administered in four divided doses of 40 mg each. The individual components of the composite capsule are discernible as separate peaks in the plasma level profiles.

EXAMPLE 5

Vinpocetine hydrochloride (10.0 kg.) and microcrystalline cellulose (Avicel-PH-101); (80.0 kg.), citric acid monohydrate (10.0 kg) were blended together in a 450 liter planetary mixer. Water (100 kg.) was added, and the mixer was run for 10 minutes until a homogeneous, plastic mass was obtained. The mass was extruded under pressure through a perforated cylinder to give cylindrical extrudates of nominally 1 mm. diameter.

The damp extrudates (in batches of 15 to 20 kg.) were placed in a spheronizer in which the rotating disc (diameter 68 cm.) rotated at 300 to 400 r.p.m. The rotation was continued for 20 minutes, and the resulting spheroids were then dried at 80° C. in a fluidized bed drier. The dried spheroids were passed over a 1.2 mm. screen, and those which passed through were subjected to a 0.5 mm. screen. The over-and under-sized spheroids were discarded.

The finished dosage form consists of a hard gelatin capsule containing a powder blend of vinpocetine and two types of spheroids. The formulation particulars are based on 30 mg per capsule, although they can be designed to provide other dosage strengths.

The vinpocetine powder blend (or first group of spheroids) provides the loading dose, (e.g. 5 mg vinpocetine).

The second and third types of spheroids are categorized as:

(1) pH sensitive coated spheroids to provide a second dose (pH>6.5) e.g. 12 mg vinpocetine.
(2) Coated spheroids to provide a third dose (4–10 hours post ingestion) e.g. 13 mg vinpocetine 1. Powder Blend
(a) Formula

| Ingredient | Quantity |
| --- | --- |
| Vinpocetine | 5 mg/capsule |
| Sodium Lauryl Sulfate, NF | 0.1 mg/capsule |
| Sodium Starch Glycolate, NF | 3 mg/capsule |
| Glutamic Acid, NF | 6 mg/capsule |
| Starch, NF | 7 mg/capsule |
| Lactose, USP | 62 mg/capsule |
| Microcrystalline cellulose, NF | 13 mg/capsule |
| Magnesium stearate, NF | 1 mg/capsule |

(b) Procedure
1. Blend the Vinpocetine, Lactose. Microcrystalline Cellulose, Starch, Glutamic Acid, Sodium Starch Glycolate, Talc Triturate and the Sodium Lauryl Sulfate into the PK blender for 20 minutes with intensifier bar running.
2. Pass the Step #1 blend through a Fitz Mill using a #1B screen, medium speed, knives forward.
3. Return the granulation from Step #2 to the PK blender and add the Magnesium Stearate and blend for 2 minutes without the intensifier bar on.

2. pH Sensitive Coated Spheroids
(i) Eudragit S System:
(a) Formula (based on 3 kg uncoated spheroids)

| Ingredients | Quantity |
| --- | --- |
| Uncoated Spheroids (10% w/w Vinpocetine) | 3.00 kg |
| Methacrylic Acid Copolymer, Type B, NF Eudragit S | 0.75 kg |
| Triacetin, NF | 0.112 kg |
| Methylene Chloride, NF | 1.99 kg |
| Isopropyl Alcohol NF | 1.64 kg |
| Water, USP, Purified | 0.50 kg |

(b) Process
Uncoated spheroids were placed in a fluidized bed coater
The Eudragit S solution was applied using a peristaltic pump
The spheroids were dried 3. Coated Spheroids
(a) Formula (based on 3 kg uncoated spheroids)

| | Quantity |
| --- | --- |
| Undercoat Ingredients | |
| Uncoated Spheroids (24% w/w vinpocetine | 3.00 kg |
| Hydroxypropyl methylcellulose, USP, 2910, 4000 cps, (e.g., Methocel E4MP) | 0.075 kg |
| Methylene Chloride, NF | 4.987 kg |
| Methanol, Anhydrous, NF | 2.963 kg |

| | Quantity |
| --- | --- |
| Overcoat Ingredients | |
| Eudragit E 30 D (Aqueous Dispersion) | 1.00 kg |
| Calcium Stearate, NF | 0.030 kg |
| Simethicone Emulsion, USP | 0.0025 kg |
| Water, USP, Purified | 0.500 kg |

(b) Process for applying undercoat
The uncoated spheroids were placed in a fluidized bed coater
Methocel E4MP solution was sprayed using a peristaltic pump
The spheroids were dried
(c) Process for applying overcoat
Eudragit E 30 D suspension containing calcium stearate was sprayed on the Methocel E4MP coated spheroids using a peristaltic pump
The spheroids were dried 4. Manufacture
Capsules were filled with the powder blend, pH sensitive coated spheroids and coated spheroids on an encapsulating machine capable of dual filling powders and spheroids.

EXAMPLE 6

The finished dosage form consists of a hard gelatin capsule containing 3 types of spheroids. The formulation particulars are based on 30 mg vinpocetine per capsule, although they can be designed to provide other dosage strengths.

The three types of spheroids are categorized as:
(1) Uncoated spheroids to provide a loading dose (e.g. 5 mg vinpocetine)
(2) pH sensitive coated spheroids to provide a second dose (pH>5.5) e.g. 12 mg vinpocetine
(3) Coated spheroids to provide a third dose (4–10 hours post ingestion) e.g. 13 mg vinpocetine 1. Uncoated Spheroids (prepared as described above in Example 5 except that 5% of the microcrystalline cellulose was replaced with Avicel RC 581)
2. Alternate pH Sensitive Coated Spheroids
Polyvinyl Acetate Phthalate (PVAP) system:
(a) Formula-(based on 3 kg uncoated spheroids)

| Ingredients | Quantity |
| --- | --- |
| Uncoated Spheroids (10% w/w vinpocetine HCl) | 3.00 kg |
| Polyvinyl Acetate Phthalate (PVAP), NF | 0.30 kg |
| Triethyl Citrate, NF | 0.03 kg |
| Stearic Acid, NF | 0.06 kg |
| Methanol Anhydrous, NF | 2.61 kg |

(b) Process
Uncoated spheroids were placed in a fluidized bed coater
The PVAP solution was applied using a peristaltic pump
The spheroids were dried
3. Coated Spheroids (prepared as described above in Example 5)
Other dosage strenghts of vinpocetine can be formulated as follows:

| Vinpocetine mg per capsule | First group of spheroids (or powder) % of dose | Second group of spheroids % of dose | Third group of spheroids % of dose |
|---|---|---|---|
| 15 to 60 | 10% to 50% | 20% to 75% | 10% to 60% |

EXAMPLE 7

Isosorbide dinitrate as a 50% triturate with lactose (60 kg) and microcrystalline cellulose (Avicel PH-101) (40 kg) are blended together in a 450 liter planetary mixer. Water (50 kg.) is added, and the mixer is run for 10 minutes until a homogeneous, plastic mass is obtained. The mass is extruded under pressure through a perforated cylinder to give cylindrical extrudates of nominally 1 mm. diameter.

The damp extrudates (in batches of 15 to 20 kg.) are placed in a spheronizer in which the rotating disc (diameter 68 cm.) rotates at 300 to 400 r.p.m. The rotation is continued for 10 minutes, and the resulting spheroids are then dried at 60° C. in a fluidized bed dried. The dried spheroids are passed over a 1.4 mm. screen, and those which pass through are subjected to a 0.7 mm. screen. The over-and under-sized spheroids are discarded.

The finished dosage form consists of a hard gelatin capsule containing a powder blend of isosorbide dinitrate and two types of spheroids. The formulation particulars are based on 40 mg per capsule, although they can be designed to provide other dosage strengths.

The isosorbide dinitrate powder blend (or first group of spheroids) provides the loading dose, (e.g., 14 mg isosorbide dinitrate (100%).

The second and third types of spheroids are categorized as:
(1) pH sensitive coated spheroids to provide a second dose (pH>6.5) e.g. 13 mg isosorbide dinitrate (100%).
(2) Coated spheroids to provide a third dose (4-10 hours post ingestion) e.g. 13 mg isosorbide dinitrate (100%).

1. Powder Blend
(a) Formula

| Ingredient | Quantity |
|---|---|
| Isosorbide dinitrate (100%) USP | 5 mg/capsule |
| Lactose, USP | 54 mg/capsule |
| Microcrystalline cellulose, NF | 15 mg/capsule |
| Magnesium stearate, NF | 1 mg/capsule |

2. pH Sensitive Coated Spheroids
(i) Eudragit S System:
(a) Formula (based on 3 kg uncoated spheroids)

| Ingredients | Quantity |
|---|---|
| Uncoated Spheroids (30% w/w isosorbide dinitrate | 3.00 kg |
| Methacrylic Acid Copolymer, Type B, NF Eudragit S | 0.75 kg |
| Triacetin, NF | 0.112 kg |
| Methylene Chloride, NF | 1.99 kg |
| Isopropyl Alcohol, NF | 1.64 kg |
| Water | 0.50 kg |

(b) Process

Uncoated spheroids are placed in a fluidized bed coater
The Eudragit S solution is applied using a peristaltic pump
The spheroids are dried
3. Coated Spheroids
(a) Formula (based on 3 kg uncoated spheroids)

| | Quantity |
|---|---|
| Undercoat Ingredients | |
| Uncoated Spheroids (30% w/w isosorbide dinitrate | 3.00 kg |
| Hydroxypropyl methylcellulose, USP, 2910, 4000 cps, (e.g., Methocel E4MP) | 0.075 kg |
| Methylene Chloride, NF | 4.987 kg |
| Methanol, Anhydrous, NF | 2.963 kg |
| Overcoat Ingredients | |
| Eudragit E 30 D (Aqueous Dispersion) | 1.00 kg |
| Calcium Stearate, NF | 0.030 kg |
| Simethicone Emulsion, USP | 0.0025 kg |
| Water, USP, Purified | 0.500 kg |

(b) Process for applying undercoat
The uncoated spheroids are placed in a fluidized bed coater
Methocel E4MP solution is sprayed using a peristaltic pump
The spheroids were dried
(c) Process for applying overcoat
Eudragit E 30 D suspension containing calcium stearate is sprayed on the Methocel E4MP coated spheroids using a peristaltic pump
The spheroids are dried
4. Manufacture
Capsules are filled with the powder blend, pH sensitive coated spheroids and coated spheroids on an encapsulating machine capable of dual filling powders and spheroids.

EXAMPLE 8

The finished dosage form consists of a hard gelatin capsule containing 3 types of spheroids. The formulation particulars are based on 40 mg isosorbide dinitrate per capsule, although they can be designed to provide other dosage strengths.

The three types of spheroids are categorized as:
(1) Uncoated spheroids to provide a loading dose (e.g. 14 mg isosorbide dinitrate)
(2) pH sensitive coated spheroids to provide a second dose (pH>5.5) e.g. 13 mg isosorbide dinitrate
(3) Coated spheroids to provide a third dose (4-10 hours post injestion) e.g. 13 mg isosorbide dinitrate
1. Uncoated Spheroids (prepared as described above)
2. Alternate pH Sensitive Coated Spheroids
Polyvinyl Acetate Phthalate (PVAP) system:
(a) Formula-(based on 3 kg uncoated spheroids)

| Ingredients | Quantity |
|---|---|
| Uncoated Spheroids (30% w/w isosorbide dinitrate) | 3.00 kg |
| Polyvinyl Acetate Phthalate (PVAP), NF | 0.30 kg |
| Triethyl Citrate, NF | 0.03 kg |
| Stearic Acid | 0.06 kg |
| Methanol, Anhydrous, NF | 2.61 kg |

(b) Process

Uncoated spheroids are placed in a fluidized bed coater

The PVAP solution is applied using a peristaltic pump

The spheroids are dried

3. Coated Spheroids (prepared as described above in Example 7)

Other dosage strengths of isosorbide dinitrate can be formulated as follows:

| Isosorbide dinitrate mg per capsule | First group of spheroids (or powder) % of dose | Second group of spheroids % of dose | Third group of spheroids % of dose |
|---|---|---|---|
| 20 to 160 | 25% to 65% | 25% to 65% | 25% to 65% |

EXAMPLE 9

Pelrinone, prepared as described in U.S. Pat. No. 4,505,910 (10 kg.) and microcrystalline cellulose (Avicel-PH-101; 90 kg.) are blended together in a 450 liter planetary mixer. Water (60 kg.) is added, and the mixer is run for 10 minutes until a homogeneous, plastic mass is obtained. The mass is extruded under pressure through a perforated cylinder to give cylindrical extrudates of nominally 1 mm. diameter.

The damp extrudates (in batches of 15 to 20 kg.) are placed in a spheronizer in which the rotating disc (diameter 68 cm.) rotates at 300 to 400 r.p.m. The rotation is continued for 10 minutes, and the resulting spheroids are then dried at 60° C. in a fluidized bed drier. The dried spheroids are passed over a 1.4 mm. screen, and those which pass through are subjected to a 0.7 mm. screen. The over-and under-sized spheroids are discarded.

The finished dosage form consists of a hard gelatin capsule containing a powder blend of pelrinone and two types of spheroids. The formulation particulars are based on 15 mg pelrinone per capsule, although they can be designed to provide other dosage strengths.

The pelrinone powder blend (or first group of spheroids) provides the loading dose, (e.g. 3 mg pelrinone).

The second and third types of spheroids are categorized as:
(1) pH sensitive coated spheroids to provide a second dose (pH>6.5) e.g. 6 mg pelrinone.
(2) Coated spheroids to provide a third dose (4–10 hours post ingestion) e.g. 6 mg pelrinone.

1. Powder Blend
(a) Formula

| Ingredient | Quantity |
|---|---|
| Pelrinone | 3 mg/capsule |
| Lactose, USP | 54 mg/capsule |
| Microcrystalline cellulose, NF | 15 mg/capsule |
| Magnesium stearate, NF | 1 mg/capsule |

2. pH Sensitive Coated Spheroids
(i) Eudragit S System:
(a) Formula (based on 3 kg uncoated spheroids)

| Ingredients | Quantity |
|---|---|
| Uncoated Spheroids (60% w/w pelrinone) | 3.00 kg |
| Methacrylic Acid Copolymer, Type B, NF Eudragit S | 0.75 kg |
| Triacetin, NF | 0.112 kg |
| Methylene Chloride, NF | 1.99 kg |
| Isopropyl Alcohol, NF | 1.64 kg |
| Water | 0.50 kg |

(b) Process

Uncoated spheroids are placed in a fluidized bed coater

The Eudragit S solution is applied using a peristaltic pump

The spheroids are dried

3. Coated Spheroids
(a) Formula (based on 3 kg uncoated spheroids)

| | Quantity |
|---|---|
| Undercoat Ingredients | |
| Uncoated Spheroids (60% w/w pelrinone) | 3.00 kg |
| Hydroxypropyl methylcellulose, USP, 2910, 4000 cps, (e.g., Methocel E4MP) | 0.075 kg |
| Methylene chloride, NF | 4.987 kg |
| Methanol, Anhydrous, NF | 2.963 kg |
| Overcoat Ingredients | |
| Eudragit E 30 D (Aqueous Dispersion) | 1.00 kg |
| Calcium Stearate, NF | 0.030 kg |
| Simethicone Emulsion, USP | 0.0025 kg |
| Water | 0.500 kg |

(b) Process for applying undercoat

The uncoated spheroids are placed in a fluidized bed coater

Methocel E4MP solution is sprayed using a peristaltic pump

The spheroids are dried (c) Process for applying overcoat

Eudragit E 30 D suspension containing calcium stearate is sprayed on the Methocel E4MP coated spheroids using a peristaltic pump The spheroids are dried 4. Manufacture Capsules are filled with the powder blend, pH sensitive coated spheroids and coated spheroids on an encapsulating machine capable of dual filling powders and spheroids.

EXAMPLE 10

The finished dosage form consists of a hard gelatin capsule containing 3 types of spheroids. The formulation particulars are based on 15 mg pelrinone per capsule, although they can be designed to provide other dosage strengths.

The three types of spheroids are categorized as:
(1) Uncoated spheroids to provide a loading dose (e.g. 3 mg pelrinone)
(2) pH sensitive coated spheroids to provide a second dose (pH>5.5) e.g. 6 mg pelrinone
(3) Coated spheroids to provide a third dose (4–10 hours post ingestion) e.g. 6 mg pelrinone 1. Uncoated Spheroids (prepared as described above)
2. Alternate pH Sensitive Coated Spheroids
Polyvinyl Acetate Phthalate (PVAP) system:
(a) Formula-(based on 3 kg uncoated spheroids)

| Ingredients | Quantity |
| --- | --- |
| Uncoated Spheroids (10% w/w pelrinone) | 3.00 kg |
| Polyvinyl Acetate Phthalate (PVAP), NF | 0.30 kg |
| Triethyl Citrate, NF | 0.03 kg |
| Stearic Acid, NF | 0.06 kg |
| Methanol, Anhydrous, NF | 2.61 kg |

(b) Process

Uncoated spheroids are placed in a fluidized bed coater

The PVAP solution is applied using a peristaltic pump

The spheroids are dried

3. Coated Spheroids (prepared as described above in Example 1)

Other dosage strengths of pelrinone can be formulated as follows:

| pelrinone mg per capsule | First group of spheroids (or powder) % of dose | Second group of spheroids % of dose | Third group of spheroids % of dose |
| --- | --- | --- | --- |
| 5 to 50 | 10% to 50% | 20% to 75% | 10% to 60% |

We claim:

1. A therapeutic composition for oral administration consisting essentially of a pharmaceutical gelatin capsule containing film coated spheroids, which spheroids prior to coating comprise 10% to 60% by weight of an vinpocetine in admixture with non-water swellable microcrystalline cellulose, and said film coating comprising (i) an undercoat selected from the group consisting of hydroxypropyl methylcellulose and hydroxypropyl methylcellulose containing as a disintegrant carboxymethylcellulose sodium or sodium starch glycolate and (ii) an overcoat consisting of a copolymer based on polymethyacrylic acid esters containing metalic stearates.

2. A therapeutic composition for once daily oral administration consisting essentially of a pharmaceutical gelatin capsule containing a powder blend of vinpocetine and two groups of coated spheroids each also containing vinpocetine wherein:
(a) said powder blend comprises 10% to 50% by weight of vinpocetine in admixture with pharmaceutical excipients for immediate release of vinpocetine to provide a loading dose of vinpocetine,
(b) said first group of spheroids comprises film coated spheroids, which spheroids prior to coating comprise 20% to 75% by weight of vinpocetine in admixture with non-water swellable cellulose, said film coating comprising (i) a copolymer based on methacrylic acid and methacrylic acid methyl ester or (ii) polyvinyl acetate phthalate, said first group of film coated spheroids having a pH sensitive coating to provide a delayed second dose of vinpocetine, and
(c) said second group of spheroids comprises film coated spheroids, which spheroids prior to coating comprise 10% to 60% by weight of vinpocetine in admixture with non-water swellable microcrystalline cellulose, and said film coating comprising (i) an undercoat selected from the group consisting of hydroxypropyl methylcellulose and hydroxypropyl methylcellulose containing as a disintegrant carboxymethylcellulose sodium or sodium starch glycolate and (ii) an overcoat consisting of a neutral copolymer based on polymethacrylic acid esters containing metallic stearates, said second group of film coated spheroids being double coated with an effective thickness to provide a further delayed third dose of vinpocetine.

3. A therapeutic composition for once daily oral administration consisting essentially of a pharmaceutical gelatin capsule containing three groups of spheroids each containing vinpocetine wherein:
(a) said first group of spheroids comprises 10% to 50% by weight of vinpocetine in admixture with non-water swellable microcrystalline cellulose for immediate release of vinpocetine to provide a loading dose of vinpocetine,
(b) said second group of spheroids comprises film coated spheroids, which spheroids prior to coating comprise 10% to 60% by weight of vinpocetine in admixture with non-water swellable cellulose, said film coating comprising (i) a copolymer based on methacrylic acid and methacrylic acid methyl ester or (ii) polyvinyl acetate phthalate, said first group of film coated spheroids having a pH sensitive coating to provide a delayed second dose of vinpocetine, and
(c) said third group of spheroids comprises film coated spheroids, which spheroids prior to coating comprise 40% to 65% by weight of vinpocetine in admixture with non-water swellable microcrystalline cellulose and said film coating comprising (i) an undercoat selected from the group consisting of hydroxypropyl methylcellulose and hydroxypropyl methylcellulose containing as a disintegrant carboxymethylcellulose sodium or sodium starch glycolate and (ii) an overcoat consisting of a neutral copolymer based on polymethacrylic acid esters containing metallic stearates, said second group of film coated spheroids being double coated with an effective thickness to provide a further delayed third dose of vinpocetine.

4. A therapeutic composition according to claims 2 or 3 wherein said gelatin capsule contains a total of from 15 mg to 60 mg vinpocetine wherein:
(a) said first group of spheroids or powder blend contains 10% to 50% of the total dose of vinpocetine,
(b) said second group of spheroids contains 20% to 75% of the total dose of vinpocetine and said spheroids are coated with 5% to 15% by weight of uncoated spheroids of a copolymer based on methacrylic acid and methacrylic acid methyl ester and triacetin, and
(c) said third group of spheroids contains 10% to 60% of the total dose of vinpocetine and said spheroids are coated with an undercoat of 2.5% to 5.5% by weight of uncoated spheroids of hydroxypropyl methylcellulose and an overcoat of 5% to 15% by weight of uncoated spheroids of a copolymer based on polymethacrylic acid esters.

5. A therapeutic composition according to claims 2 or 3 wherein said gelatin capsule contains a total of from 15 mg to 60 mg vinpocetine, wherein:
(a) said first group of spheroids or powder blend contains 10% to 50% of the total dose of vinpocetine,
(b) said second group of spheroids contains 20% to 75% of the total dose of vinpocetine and said spheroids are coated with a copolymer based on methacrylic acid and methacrylic acid methyl ester and triacetin, and
(c) said third group of spheroids contains 10% to 60% of the total dose of vinpocetine and said spheroids are coated with an undercoat of hydroxypropyl methylcellulose and an overcoat of a copolymer based on polymethacrylic acid esters.

6. A therapeutic composition according to claim 5 wherein said gelatin capsule contains a total of 30 mg vinpocetine, wherein:
(a) said first group of spheroids contains 10% to 50% of the total dose of vinpocetine,
(b) said second group of spheroids contains 25% to 50% of the total dose of vinpocetine and said spheroids are coated with the copolymer based on methacrylic acid and methacrylic acid methyl ester and triacetin, and
(c) said third group of spheroids contains 25% to 50% of the total dose of vinpocetine and said spheroids are coated with an undercoat of hydroxypropyl methylcellulose and an overcoat of a copolymer based on polymethacrylic acid esters.

7. A therapeutic composition according to claim 3 comprising a pharmaceutical hard gelatin capsule containing three groups of spheroids containing vinpocetine, wherein:
(a) said first group of spheroids comprising uncoated spheroids contains vinpocetine for maximum release thereof within a period of two hours after ingestion,
(b) said second group of spheroids contains vinpocetine coated with a pH sensitive coat comprising (i) a copolymer based on methacrylic acid and methacrylic acid methyl ester or (ii) polyvinyl acetate phthalate, said coat having an effective thickness to provide a maximum release of medicinal substance in a period of 2 to 6 hours after ingestion, and
(c) said third group of spheroids contains vinpocetine coated with an undercoat of hydroxypropyl methylcellulose and an overcoat of the copolymer based on polymethacrylic acid esters containing metallic stearates, said coats having an effective thickness to provide a maximum release of medicinal substance 4 to 10 hours after ingestion.

8. A therapeutic composition according to claim 1 wherein the two said coats having an effective thickness to provide a maximum release of medicinal substance 4 to 10 hours after ingestion.

* * * * *